United States Patent [19]
Kolpin et al.

[11] 4,429,001
[45] Jan. 31, 1984

[54] SHEET PRODUCT CONTAINING SORBENT PARTICULATE MATERIAL

[75] Inventors: Barbara E. Kolpin, River Falls, Wis.; David C. Brownlee, White Bear Lake, Minn.

[73] Assignee: Minnesota Mining and Manufacturing Company, St. Paul, Minn.

[21] Appl. No.: 354,806

[22] Filed: Mar. 4, 1982

[51] Int. Cl.³ .......................... D04G 1/56; D04G 1/72
[52] U.S. Cl. ..................................... 428/283; 428/296; 428/297; 428/303; 428/323; 428/327; 428/332; 428/338; 428/903; 428/913
[58] Field of Search ............... 428/283, 296, 297, 303, 428/323, 327, 332, 338, 903, 913

[56] References Cited
U.S. PATENT DOCUMENTS

| | | | |
|---|---|---|---|
| 2,881,769 | 4/1959 | Touey | 131/208 |
| 2,917,054 | 12/1959 | Touey | 131/208 |
| 3,008,472 | 11/1961 | Touey | 131/208 |
| 3,661,302 | 5/1972 | Braun | 222/226 |
| 3,670,731 | 6/1972 | Harmon | 128/284 |
| 3,823,057 | 7/1974 | Roberts et al. | |
| 3,971,373 | 7/1976 | Braun | 128/146.2 |
| 3,981,100 | 9/1976 | Weaver et al. | 47/58 |
| 3,993,553 | 11/1976 | Assarsson et al. | 204/159 |
| 3,998,988 | 12/1976 | Shimomai et al. | 428/400 |
| 4,011,067 | 3/1977 | Carey, Jr. | 55/354 |
| 4,103,062 | 7/1978 | Aberson et al. | 428/283 |
| 4,105,033 | 8/1978 | Chatterjee et al. | 128/285 |
| 4,118,531 | 10/1978 | Hauser | 428/224 |
| 4,160,059 | 7/1979 | Samejima | 428/288 |
| 4,235,237 | 11/1980 | Mesek et al. | 128/284 |

OTHER PUBLICATIONS

Wente, Van A. "Superfine Thermoplastic Fibers", Ind. Eng. Chemistry, vol. 48, pp. 1342 et seq. (1956).
Report 4364 Naval Research Laboratories, May 25, 1954, "Manufacture of Superfine Organic Fibers", by Wente, Van A.; Boone, E. L.; and Fluharty, C. D.

*Primary Examiner*—James C. Cannon
*Attorney, Agent, or Firm*—D. M. Sell; J. A. Smith; R. R. Tamte

[57] ABSTRACT

New sorbent sheet products are prepared comprising a coherent web of entangled blown fibers prepared by extruding liquid fiber-forming material into a high-velocity gaseous stream and an array of super absorbent polymeric particles dispersed within the web.

25 Claims, 4 Drawing Figures

SHEET PRODUCT CONTAINING SORBENT PARTICULATE MATERIAL

BACKGROUND OF THE INVENTION

Many prior workers have sought to increase the sorbency of fibrous web products by addition of "super absorbent" particles, e.g., modified starch or other polymeric particles which sorb and retain under pressure large volumes of liquids, especially aqueous liquids. The previous products prepared by such additions all have had significant limitations. For example, one commercial product, which comprises sorbent particles adhered between two sheets of tissue paper, decomposes in use, whereupon the sorbent particles are washed out of the product and into liquid being treated. Another commercial product, comprising a rather stiff open-mesh fabric or cheese cloth to which essentially a single layer of sorbent particles is adhered, sorbs only limited amounts of liquid.

A different product taught in U.S. Pat. No. 4,103,062 is made by dispersing particles in an air-laid cellulosic fiber web and densifying the web with heat and pressure to increase its strength. However, this product sorbs only a limited amount of liquid, because of the nonexpansible nature of the densified web, and because sorbent particles at the edge of the web swell upon initial liquid intake and prevent permeation of additional liquid into internal parts of the web. U.S. Pat. No. 4,105,033 seeks to avoid such edge blockage by distributing the sorbent particles in spaced layers separated by layers of fibers, but such a construction requires added processing steps and is subject to delamination. In other products sorbent particles are simply cascaded into a loose fibrous web (see U.S. Pat. No. 3,670,731), but both U.S. Pat. Nos. 4,103,062 and 4,105,033 note that it is difficult to deposit the particles uniformly, and the particles tend to move within the web during subsequent processing, storage, shipment or use of the web and thereby develop nonuniform properties.

U.S. Pat. No. 4,235,237 teaches a different approach in which a fibrous web is sprayed, immersed or otherwise contacted with sorbent material dispersed in a volatile liquid. Vaporization of the volatile liquid leaves a web in which sorbent particles envelop the fibers, principally at fiber intersections. Disadvantages of this approach include the need for multiple steps to prepare the product, limitations on amount of sorbent that can be added to the web, brittleness of the dried webs, and the tendency for sorbent material to be concentrated at the web surface.

SUMMARY OF THE INVENTION

The present invention provides a new sorbent sheet product with unique capabilities beyond those of any known prior-art product. Briefly, this new sheet product comprises a coherent web of blown fibers, and an array of solid high-sorbency liquid-sorbent polymeric particles dispersed within the web. The blown fibers are prepared by extruding liquid fiber-forming material into a high-velocity gaseous stream, where the extruded material is attenuated and drawn into fibers. A stream of fibers is formed, which is collected, e.g., on a screen disposed in the stream, as an entangled coherent mass. According to the invention sorbent particles may be introduced into the stream of fibers, e.g., in the manner taught in U.S. Pat. No. 3,971,373, and the mixture of fibers and particles is collected as an entangled coherent mass in which the sorbent particles are entrapped or otherwise physically held. A particle-filled fibrous web is formed in essentially one step, and the only further processing required may be simply cutting to size and packaging for use.

A sheet product of the invention is integral and handleable both before and after immersion in liquid, because the collected blown fibers are extensively tangled or snarled and form a strong coherent web, and the sorbent particles are lastingly held and retained within this web.

Large quantities of liquid can be sorbed, with the amount dependent principally on the sorption capacity of the individual sorbent particles. Liquid is sorbed by sorbent particles located in even the inner parts of the sheet product, apparently because the sorbent particles are held apart by the web structure, allowing liquid to surround individual particles before swelling occurs. The fibers of the web are preferably wet by the liquid being sorbed, e.g., as a result of use of a fiber-forming material that is wet by the liquid or by addition of a surfactant during the web-forming process, which further assists sorption.

The sorbent particles swell and expand in size during sorption, and although the blown fibers are extensively entangled, the web of fibers expands as the particles expand and the sorbed liquid tends to be retained in the product even when the product is subjected to pressure.

DETAILED DESCRIPTION

Figure 1:
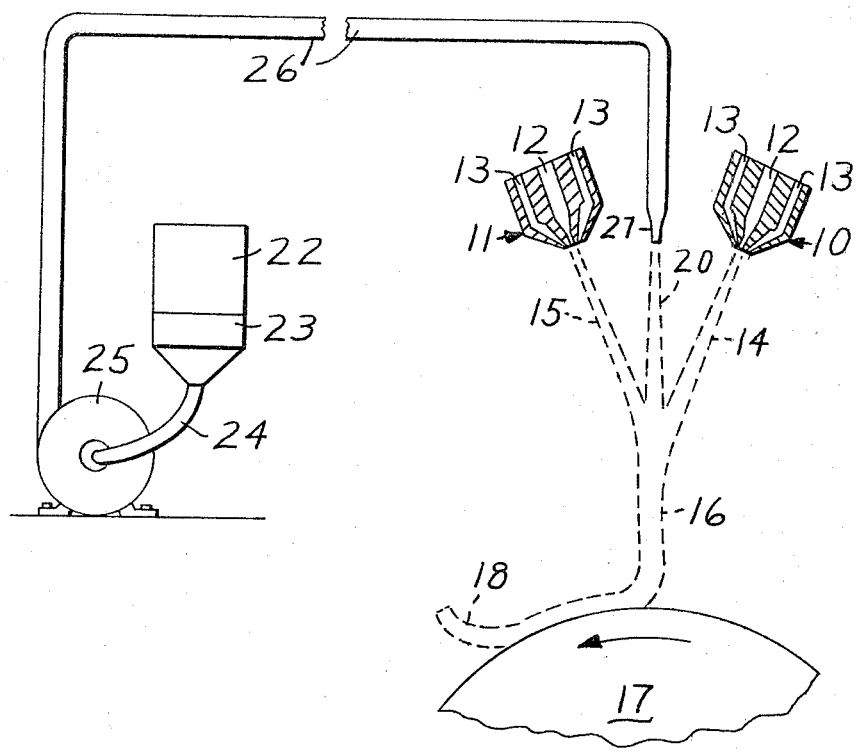
FIG. 1 is a schematic diagram of apparatus used in practicing the present invention.
Figure 2:
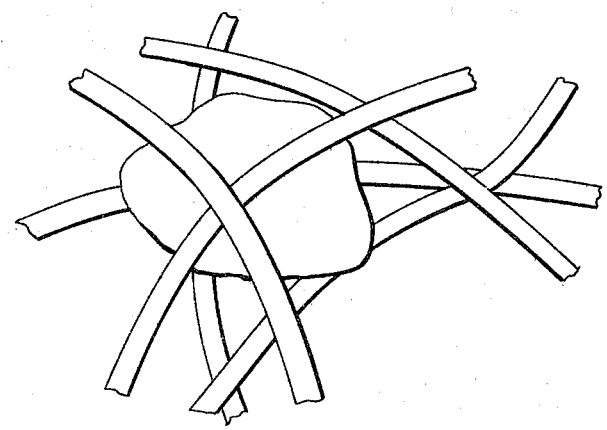
FIG. 2 is a greatly enlarged sectional view of a portion of a sheet product of the invention.

A representative apparatus useful for preparing sheet product of the invention is shown schematically in FIG. 1. The apparatus is generally similar to that taught in U.S. Pat. No. 3,971,373 for preparing a particle-loaded web of melt-blown fibers. Part of the apparatus for forming melt-blown fibers is described in Wente, Van A., "Superfine Thermoplastic Fibers" in *Industrial Engineering Chemistry*, Vol. 48, p. 1342 et seq. (1956), or in Report No 4364 of the Naval Research Laboratories, published May 25, 1954, entitled "Manufacture of Superfine Organic Fibers," by Wente, V. A.; Boone, C. D.; and Fluharty, E. L. The illustrated apparatus includes two dies 10 and 11 which include a set of aligned parallel die orifices 12 through which the molten polymer is extruded, and cooperating air orifices 13 through which heated air is forced at a very high velocity. The air draws out and attenuates the extruded polymeric material, and after a short travel in the gaseous stream, the extruded material solidifies as a mass of fibers. According to the present invention, two dies are preferably used and arranged so that the streams 14 and 15 of fibers issuing from them intersect to form one stream 16 that continues to a collector 17. The latter may take the form of a finely perforated cylindrical screen or drum, or a moving belt. The collected web 18 of microfibers is then removed from the collector and wound in a storage roll. Gas-withdrawal apparatus may be positioned behind the collector to assist in deposition of fibers and removal of gas.

The apparatus shown in FIG. 1 also includes apparatus for introducing sorbent particles into the sheet product of the invention. Desirably this apparatus introduces a stream 20 of the sorbent particles which intercepts the two streams of melt-blown fibers at the latter's point of intersection. Such an arrangement is believed to be capable of providing a maximum loading of particles into the collected fibrous web. Alternatively a single die may be used with one or more particle streams arranged to intersect the stream of fibers issuing from the die. The streams of fibers and sorbing particles may travel in horizontal paths as shown in FIG. 1, or they may travel vertically so as to generally parallel the force of gravity.

In the representative apparatus illustrated in FIG. 1, the apparatus for feeding sorbent particles into the stream of fibers comprises a hopper 22 for storing the particles; a metering device 23, such as a magnetic valve or metering device described in U.S. Pat. No. 3,661,302, which meters particles into a conduit 24 at a predetermined rate; an air impeller 25 which forces air through a second conduit 26 and which accordingly draws particles from the conduit 24 into the second conduit 26; and a nozzle 27 through which the particles are ejected as the particle stream 20. The nozzle 27 may be formed, for example, by flattening the end of a cylindrical tube to form a wide-mouthed thin orifice. The amount of particles in the particle stream 20 is controlled by the rate of air flow through the conduit 26 and by the rate of particles passed by the metering device 23.

Melt-blown fibers are greatly preferred for sheet products of the invention, but solution-blown fibers in which the fiber-forming material is made liquid by inclusion of a volatile solvent can also be used. U.S. Pat. No. 4,011,067 describes useful apparatus and procedures for preparing a web of such fibers; however, in preparing sheet products of this invention fiber-forming material is generally extruded through a plurality of adjacent orifices rather than the single orifice shown in the patent.

The particles are preferably introduced into the fiber stream at a point where the fibers have solidified sufficiently that the fibers will form only a point contact with the particles (as taught in U.S. Pat. No. 3,971,373). However, the particles can be mixed with the fibers under conditions that will produce an area contact with the particles.

Once the sorbent particles have been intercepted in the fiber stream, a process for making the sheet product of the invention is generally the same as the process for making other blown fiber webs; and the collectors, methods of collecting, and methods of handling collected webs are generally the same as those for making non-particle-loaded blown fiber webs.

The layer of fibers and particles formed in any one revolution, and a completed sheet product of the invention may vary widely in thickness. For most uses of sheet products of the invention, a thickness between about 0.05 and 2 centimeters is used. For some applications, two or more separately formed sheet products of the invention may be assembled as one thicker sheet product. Also sheet products of the invention may be prepared by depositing the stream of fibers and sorbent particles onto another sheet material such as a porous nonwoven web which is to form part of the eventual sheet product. Other structures, such as impermeable films, can be laminated to a sheet product of the invention through mechanical engagement, heat bonding, or adhesives.

Sheet products of the invention may be further processed after collection, e.g., compacting through heat and pressure to control sheet caliper, to give the sheet product a pattern or to increase the retention of sorbent particles. Other fibers besides blown fibers may be introduced into the sheet product in the manner taught in U.S. Pat. No. 4,118,531. For example, crimped bulking fibers as described in that patent may be mixed with blown fibers together with sorbent particles to prepare a more lofty or lightweight sheet product.

The blown fibers are preferably microfibers, averaging less than about 10 micrometers in diameter, since such fibers offer more points of contact with the particles per unit volume of fiber. Very small fibers, averaging less than 5 or even 1 micrometer in diameter, may be used, especially with sorbent particles of very small size. Solution-blown fibers have the advantage that they may be made in very fine diameters, including less than one micrometer. Larger fibers, e.g., averaging 25 micrometers or more in diameter, may also be prepared, especially by the melt-blowing process.

Figure 3:
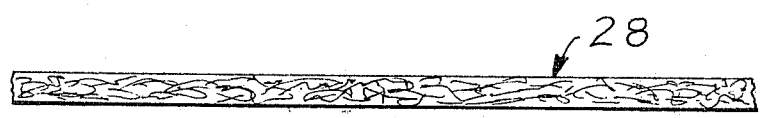
FIGS. 3A and 3B are side views of a sheet product of the invention, FIG. 3A showing the sheet product before use and FIG. 3B showing the sheet product after it has been used to sorb a substantial amount of liquid.
Figure 4:
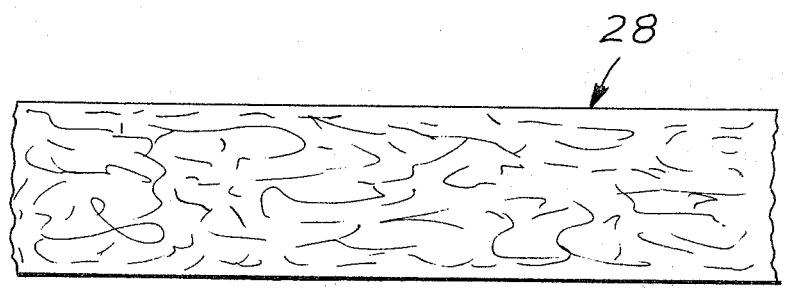

Blown fibrous webs are characterized by an extreme entanglement of the fibers, which provides coherency and strength to a web and also adapts the web to contain and retain particulate matter. The aspect ratio (ratio of length to diameter) of blown fibers approaches infinity, though the fibers have been reported to be discontinuous. The fibers are long and entangled sufficiently that it is generally impossible to remove one complete fiber from the mass of fibers or to trace one fiber from beginning to end. Despite such entanglement, a sheet product as represented by the sheet 28 in FIG. 3A will expand greatly in size during sorption, as represented in FIG. 3B. Sheet products of the invention generally can expand at least 3 times their original thickness during sorption, and more typically expand 5 or 10 or more times their original thickness.

The fibers may be formed from a wide variety of fiber-forming materials. Representative polymers for forming melt-blown fibers include polypropylene, polyethylene, polyethylene terephthalate, and polyamides. Representative polymers for forming solution-blown fibers include polymers or copolymers of vinyl acetate, vinyl chloride, and vinylidene fluoride. Inorganic materials also form useful fibers. Fibers of different fiber-forming materials may be used in the same sheet product in some embodiments of the invention, either in mixture in one layer or in different layers.

Many of the fiber-forming materials form hydrophobic fibers, which can be undesirable in water-sorbing sheet products. To improve the sheet product for such a use, a surfactant in powder or liquid form may be introduced into the sheet product, as by mixing powders with the sorbent particles before they are introduced into the web or spraying liquids onto the web after it is formed. Useful surfactants, which typically comprise molecules having oleophilic and hydrophilic moieties, include dioctyl ester of sodium sulfosuccinate and alkylaryl polyether alcohol. A small amount of the surfactant, such as 0.05 to 1 weight-percent of the sheet product, will generally provide adequate hydrophilicity, but larger amounts can be used. Use of oleophilic fibers together with water-sorbing particles can have the advantage of dual absorption, in that the fibrous web sorbs organic liquids such as oils while the particles sorb water.

As indicated above, the sorbent particles used in the invention are generally super absorbent particles, which rapidly absorb and retain under pressure larger quantities of liquids. The preferred particles for sorbing water comprise modified starches, examples of which are described in U.S. Pat. No. 3,981,100, and high-molecular-weight acrylic polymers containing hydrophilic groups. A wide variety of such water-insoluble water-sorbing particles are available commercially, and they typically sorb 20 or more times their weight of water and preferably 100 or more times their weight of water. The amount of water sorbed declines as impurities are included in the water. Alkylstyrene sorbent particles (such as marketed by Dow Chemical Company under the trademark "Imbiber Beads") are useful for sorbing liquids other than water. They tend to sorb 5 or 10 times or more their weight of such liquids. In general the sorbent particles should sorb at least their own weight of liquid.

The sorbent particles may vary in size, at least from 50 to 3000 micrometers in average diameter. Preferably, the particles are between 75 and 1500 micrometers in average diameter.

The volume of sorbent particles included in a sheet product of the invention will depend on the particular use to be made of the product and will involve balancing the amount of sorbency desired with properties such as integrity or strength of the web, or desired web thickness. Generally sorbent particles account for at least 1, and more typically at least 20, volume-percent of the solid content of the sheet product ("solid content" is used to contrast with bulk volume and refers to the physical components of the sheet product and not the voids or interstices between those components). However amounts under 10 or 20 volume-percent are useful and have the advantage that they are retained in the web even more completely than particles at higher loadings are retained. Where high sorbency is desired, the sorbent particles generally account for at least 50 volume-percent of the solid content of the sheet product. One of the advantages of the invention is that high particle-loadings can be achieved, though there is seldom need for particles in excess of 90 volume-percent.

Sheet material of the invention has a variety of uses, including uses listed in the prior art such as bandages, diapers, incontinent pads, and sanitary napkins.

The invention will be further illustrated by the following examples.

EXAMPLES 1 AND 2

Two sets of sheet product of the invention were prepared from polypropylene microfibers that averaged about 5 micrometers in diameter, sorbent particles comprising a synthetic high-molecular-weight acrylic polymer containing hydrophilic carboxylate groups ("Permasorb 29," supplied by National Starch and Chemical Corporation), and surfactant particles of dioctyl ester of sodium sulfosuccinate ("Aerosol OT-B" from American Cyanamid). The sorbent particles and surfactant particles (in the amounts stated below) were mixed together and introduced into a stream of the microfibers using apparatus as shown in FIG. 1. The die orifices of the two dies were separated from one another by 6 inches (15 centimeters), the dies were arranged to project fiber streams at an angle of 30° to the vertical, and the fiber streams intersected at a variable distance about 5–10 inches (12–25 centimeters) from the die orifices and continued to a collector surface located 12 inches (30 centimeters) from the die orifices. Polymer was extruded through the die orifices at a rate of about 4 pounds per hour per inch (0.7 kilogram/hour/centimeter) width of die, and air heated to 700° F. (370° C.) was forced through the hot air orifices of the dies.

The prepared sheet products were immersed in tap water and the sorbency of the products measured (weight of sheet product after immersion ("wet") minus weight before immersion ("dry") divided by weight before immersion). Results and proportions of components are given in Table I below.

TABLE I

| Ex. No. | Amount of Sorbent Particles | | Amount of Surfactant | Total Weight of Sheet Product (grams per square meter) | Thickness of Sheet Product | | Water Sorbency |
| --- | --- | --- | --- | --- | --- | --- | --- |
| | Weight ratio of fibers and particles | Volume-percent of solid content of web occupied by sorbent particles (percent) | Weight-percent of sheet product accounted for by surfactant (percent) | | Dry Inches (Centimeters) | Wet | Ratio of weight of water sorbed to weight of sheet product |
| 1 | 1:2.9 | 62 | 0.8 | 510 | 0.12 (0.3) | 0.7 (1.8) | 33 |
| 2 | 1:4.4 | 71 | 0.8 | 700 | 0.1 (0.25) | 1.4 (3.6) | 59 |

EXAMPLES 3–11

Sheet product of the invention was prepared comprising polypropylene microfibers averaging about 5 micrometers in diameter and two different varieties of sorbent particles, one being a modified starch ("Waterlock A-100" supplied by Grain Processing Corporation) and the second being a synthetic high-molecular-weight acrylic polymer containing hydrophilic carboxylate groups ("Permasorb 20," supplied by National Starch and Chemical Corporation). The sorbent particles were included in different amounts as shown in Table II below. The total amount of water sorbed by immersing each sample of sheet product in tap water for, respectively, 5 minutes and 20 minutes was measured and is reported in Table II as a ratio of grams of water sorbed per gram of sheet product. The amount of water sorbed and retained after the sheet product was immersed for, respectively, 5 minutes and 18 hours, and then laid on a cellulose paper towel for 30 seconds was also measured and is reported as a ratio of grams of water per grams of sheet product. A percent of theoretical sorption is also reported, which is a ratio of the water sorbed and retained (after 20 minute immersion and laying on a paper towel) to the amount of water which the sorbent particles will sorb when immersed in water by themselves.

TABLE II

| Example No. | Total Weight of Sheet Product (grams/m²) | Weight-Percent Sorbent Particles (Percent) | Ratio of Weight of Water Sorbed After Immersion for Time Shown to Weight of Sheet Product | | Ratio of Weight of Water Sorbed and Retained After Sheet Product Immersed for Time Shown and Laid on Paper Towel to Weight of Sheet Product | | Ratio of Sorption by Sheet Product to Sorption by Sorbent Particles (Percent) |
|---|---|---|---|---|---|---|---|
| | | | 5 Min | 20 Min | 20 Min | 18 Hour | |
| 3 | 100 | 30 | 16 | 17 | 15 | 13 | 68 |
| 4 | 125 | 42 | 25 | 26 | 23 | 25 | 75 |
| 5 | 225 | 68 | 40 | 43 | 39 | 48 | 79 |
| 6 | 260 | 73 | 46 | 52 | 48 | 59 | 90 |
| 7 | 250 | 70 | 34 | 34 | 33 | 43 | 65 |
| 8 | 23 | 40 | 36 | 46 | 29 | — | 69 |
| 9 | 27 | 50 | 42 | 46 | 37 | 31 | 70 |
| 10 | 42 | 53 | 38 | 46 | 37 | 39 | 66 |
| 11 | 140 | 85 | 41 | 45 | 41 | — | 46 |

What is claimed is:

1. A sorbent sheet product comprising a coherent web of entangled melt blown fibers and an array of solid high-sorbency liquid-sorbent polymeric particles uniformly dispersed and physically held within the web, said particles swelling upon sorption of liquid and the web expanding as the particles swell with sorbed liquid.

2. A sheet product of claim 1 in which the sorbent particles comprise at least 20 volume-percent of the solid content of the sheet product.

3. A sheet product of claim 1 in which the sorbent particles comprise at least 50 volume-percent of the solid content of the sheet product.

4. A sheet product of claim 1 in which the blown fibers comprise microfibers averaging less than about 10 micrometers in diameter.

5. A sheet product of claim 1 in which the sorbent particles are capable of sorbing about 20 or more times their own weight of a liquid.

6. A sheet product of claims 1, 2, 3, 4, or 5 in which surfactant particles which assist wetting of the web by a liquid to be sorbed are also dispersed within the web of fibers.

7. A sheet product of claims 1, 2, 3, 4 or 5 in which the sorbent particles are selected from modified starches and acrylic polymers having hydrophilic functionality.

8. A sorbent sheet product comprising a coherent web of entangled melt-blown organic polymeric microfibers averaging less than about 20 micrometers in diameter and an array of solid sorbent particles dispersed and physically held in the web, the particles accounting for at least about 20 volume-percent of the solid content of the sheet product and being capable of sorbing about 20 or more times their weight of a liquid, and the web being capable of expanding at least 3 times its original thickness as the particles sorb liquid.

9. A sheet product of claim 8 in which the sorbent particles account for at least about 50 volume-percent of the solid content of the sheet product.

10. A sheet product of claim 8 in which the microfibers are selected from polypropylene, polyethylene, polyethylene terephthalate and polyamides.

11. A sheet product of claim 8 in which the sorbent particles are selected from modified starches and acrylic polymers having hydrophilic functionality.

12. A sheet product of claim 8 in which the sorbent particles range between about 50 and 3000 micrometers in diameter.

13. A sorbent sheet product comprising a coherent web of entangled melt-blown organic polymeric microfibers averaging less than about 10 micrometers in diameter, an array of solid sorbent particles uniformly dispersed and physically held within the web, and a surfactant which assists wetting of the web by water, the sorbent particles accounting for at least about 20 volume-percent of the solid content of the sheet product, and sorbing about 20 or more times their weight of water, and the sheet product being capable of expanding at least 3 times its original thickness as the particles sorb water.

14. A sheet product of claim 13 in which the sorbent particles are selected from modified starches and acrylic polymers having hydrophilic functionality.

15. A sheet product of claim 14 in which the sorbent particles range between about 50 and 3000 micrometers in diameter.

16. A sheet product of claim 13 in which the sorbent particles account for at least about 50 volume-percent of the solid content of the sheet product.

17. A sheet product of claim 1 which includes other fibers mixed with the blown fibers.

18. Sheet product of claim 17 in which the other fibers comprise crimped fibers which increase the loft of the sheet product.

19. A sheet product of claim 8 which includes other fibers mixed with the melt-blown organic polymeric microfibers.

20. Sheet product of claim 19 in which the other fibers are crimped fibers that increase the loft of the sheet product.

21. A sheet product of claim 13 which includes other fibers mixed with the melt-blown organic polymeric microfibers.

22. A sheet product of claim 21 in which the other fibers are crimped fibers that increase the loft of the sheet product.

23. A sheet product of claims 1, 2, 3, 4, 5, 17 or 18 in which a surfactant which assists wetting of the web by a liquid to be sorbed is included in the web.

24. A sheet product of claim 8, 9, 19 or 20 in which a surfactant which assists wetting of the web by a liquid to be sorbed is included in the web.

25. A sheet product of claim 13, 21 or 22 in which the surfactant comprises particles that are mixed with the sorbent particles.

* * * * *

UNITED STATES PATENT AND TRADEMARK OFFICE
CERTIFICATE OF CORRECTION

PATENT NO. : 4,429,001

DATED : January 31, 1984

INVENTOR(S) : Barbara E. Kolpin, et al

It is certified that error appears in the above-identified patent and that said Letters Patent is hereby corrected as shown below:

Claim 8, line 3 (Col. 7, line 45), "20" should read --10--.

Signed and Sealed this

Fifteenth Day of October 1985

[SEAL]

Attest:

DONALD J. QUIGG

Attesting Officer

Commissioner of Patents and
Trademarks—Designate